United States Patent [19]

Stevens

[11] 4,351,909

[45] Sep. 28, 1982

[54] HIGH PERFORMANCE ION-EXCHANGE COMPOSITION

[75] Inventor: Timothy S. Stevens, Midland, Mich.

[73] Assignees: The Dow Chemical Co., Midland, Mich.; Dionex Corporation, Sunnyvale, Calif.

[21] Appl. No.: 265,762

[22] Filed: May 21, 1981

Related U.S. Application Data

[63] Continuation of Ser. No. 80,909, Oct. 1, 1979, abandoned.

[51] Int. Cl.³ .................... B01J 39/06; B01J 41/06; B01J 47/02
[52] U.S. Cl. ..................................... 521/28; 521/29
[58] Field of Search ................................. 521/28, 29

[56] References Cited

U.S. PATENT DOCUMENTS

| | | | |
|---|---|---|---|
| 3,485,658 | 12/1969 | Iler | 117/69 |
| 3,488,922 | 1/1970 | Kirkland | 55/67 |
| 3,847,857 | 11/1974 | Haag et al. | 521/28 |
| 4,101,460 | 7/1978 | Small et al. | 521/29 |
| 4,119,580 | 10/1978 | Smith, Jr. et al. | 521/28 |
| 4,200,695 | 3/1980 | Chong et al. | 521/28 |

FOREIGN PATENT DOCUMENTS 1045978 12/1958 Fed. Rep. of Germany .

OTHER PUBLICATIONS

Grubhofer, Angew. Chemie 71:215-217, (1959) (English translation only).

Primary Examiner—Joseph L. Schofer
Assistant Examiner—Peter F. Kulkosky
Attorney, Agent, or Firm—Douglas N. Deline

[57] ABSTRACT

An ion-exchange composition comprising a substrate of a macroporous synthetic resin having ion-exchanging sites at least on its available surface; and finely divided, synthetic resin particles having a volume average diameter less than 0.1 micron and greater than about 0.005 micron and having, at least on their outer surfaces, ion-exchanging sites which attract the ion-exchanging sites of the substrate, irreversibly attached as a monolayer to the available surface of the substrate. The composition is used for removal and separation of ions, and is especially useful in liquid ion-exchange chromatography.

9 Claims, 2 Drawing Figures

HIGH PERFORMANCE ION-EXCHANGE COMPOSITION

CROSSREFERENCE TO RELATED APPLICATION

This is a continuation of application Ser. No. 80,909, filed Oct. 1, 1979, now abandoned.

BACKGROUND OF THE INVENTION

1. Field of the Invention

The invention pertains to an ion-exchange resinous material useful for practicing high performance ion-exchange chromatography.

2. Prior Art

Materials for performing liquid chromatographic analyses are known where only the thin outer surfaces of the chromatographic support materials are available for actively exchanging ions with liquid media. For example: Small et al., in U.S. Pat. No. 4,101,460 (1978) describe the preparation and use of an ion-exchange composition comprising Component A, an insoluble synthetic resin substrate having ion-exchanging sites at least on its available surface having irreversibly attached thereto Component B, a finely divided insoluble material of from about 0.1 to about 5 microns median diameter. Macroporous resins may be used for Component A.

Smith et al. in U.S. Pat. No. 4,119,580 describe an improved method of forming agglomerated ion-exchange particles including the particles claimed in U.S. Pat. No. 4,101,460.

SUMMARY OF THE INVENTION

The invention is an ion-exchange composition comprising:

Component A, a macroporous substrate which consists essentially of synthetic resin, having ion-exchanging sites at least on its available surface, having a volume average pore diameter of X; and Component B, finely divided synthetic resin particles having a volume average diameter (D) less than 0.1 micron and greater than about 0.005 micron, and having ion-exchanging sites, at least on their outer surfaces, which attract available sites of Component A, wherein the particles of Component B are irreversibly attached as a monolayer to the available surface of Component A; provided that the ratio X/D is from about 4 to about 30.

The ion-exchange composition of the invention may be used in strongly basic or acidic media, and the monolayer has been found to be highly stable against detachment by shear forces. The invention exhibits improved levels of performance and capacity and other benefits over previously known ion-exchange compositions.

DETAILED DESCRIPTION OF THE INVENTION

Figure 1:
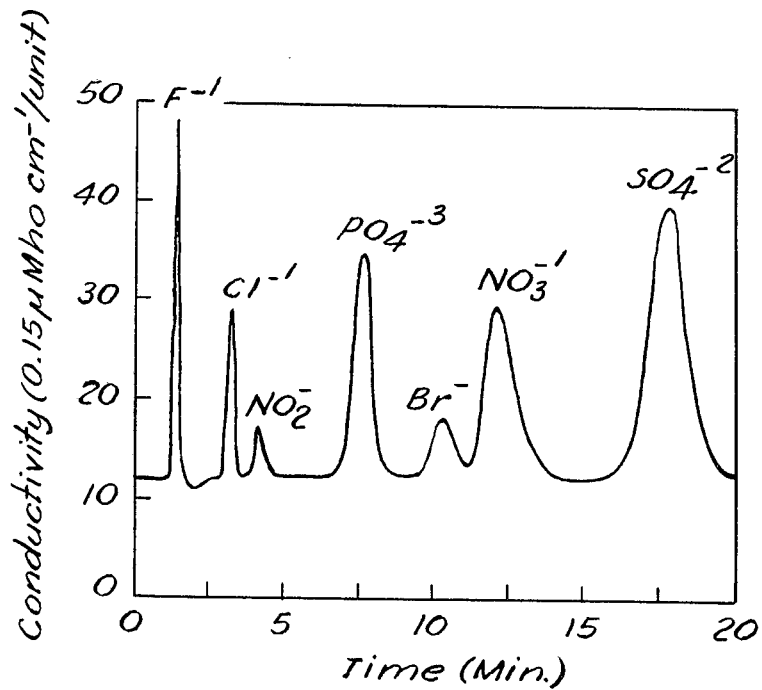
FIG. 1 is a chromatogram performed on a standard of seven anions using a column of the ion-exchange composition of the present invention.

The inventive composition comprises a macroporous substrate, hereinafter designated Component A, which consists essentially of synthetic resin material chosen to be insoluble in any solvent system with which it may be later contacted. It may be utilized in any shape, form, or size and is suitably comprised of finely divided particles of about 2 to about 75 microns particle size, preferably of about 2 to about 30 microns, most preferably from about 5 to about 10 microns.

Component A is suitably derived from any macroporous synthetic resin material having ion-exchanging sites at least on its available surface (hereinafter "available sites"). A wide variety of condensation and addition "backbone" polymers bearing ion-exchanging sites of the form desired (i.e., anion- or cation-exchanging) are known to the art. These synthetic resins and their preparation are amply described by Wheaton and Hatch in Chapter 6 of "Ion Exchange", Vol. 2, J. Marinsky Ed. (New York 1969). For example, synthetic ion-exchange resins such as poly(phenol-formaldehyde), polyacrylic or polymethacrylic acid or nitrile, and particularly poly(vinylaromatic) resins such as those derived from styrene, alpha-methylstyrene, chlorostyrene, chloromethylstyrene, vinyltoluene, vinylnaphthalene or vinylpyridine, all of which resins have been suitably cross-linked to render them insoluble in the solvents with which they will be contacted and which bear desired ion-exchanging sites, are suitable macroporous synthetic resins from which Component A may be formed.

The term "macroporous" as used in the specification, examples and in the claims herein refers to a porous resin of volume average pore diameter greater than about 200 Å (0.02μ) without reference to the resin structure or method of producing the resin.

In the preferred embodiment, Component A comprises a macroporous copolymeric resin bead having a unique porous structure prepared by suspension polymerization of a monomer and a cross-linking agent in the presence of a solvent which is capable of dissolving the monomers but is a poor solvent for the cross-linked polymer being formed. Such unique macroporous resin beads are well-known and may be produced according to the procedures taught in U.S. Pat. No. 3,418,262; 3,509,078; 3,551,358; 3,637,535; and 3,586,646.

As regards the porous nature of Component A, it has been found that the quantity of pores permeating Component A and the size of those pores in relation to the size of Component B determine the ion-exchange capacity of the resulting resin. Suitable Component A particles are those having a volume average pore diameter (X) selected to provide a significant proportion of available surface internally relative to that on the external surface of Component A. Additionally, Component A particles are suitably chosen so that the volume average pore diameter is sufficiently large that excessive plugging of individual pores by Component B particles does not occur. This excessive plugging presents a macroporous resin substantially without the benefit of the useful properties disclosed by the present invention. Referring to the volume average diameter of Component B as D, the preferred ratio of X/D should be at least about 4 in order to satisfy these requirements. Based on the minimum practical Component B volume average diameter of about 0.005μ it is seen that a minimum volume average pore diameter of about 0.02μ (200 Å) is preferred according to the instant invention.

A maximum preferred X/D ratio is suitably selected by consideration of additional operational factors. For example, additional increases in volume average pore size produce relatively greater increases of pore volume that pore internal surface area because pore volume is a function of the square of the pore diameter and surface area is a linear function of pore diameter. The ion-exchange capacity of the resulting resin is improved by increasing the amount of available surface having Component B attached thereto in contact with chromatographic solutions employed, and conversely such ion-exchange capacity is reduced by increasing the permeability of the resin, i.e., increasing the flow of chromatographic solutions through the resin having minimum contact with Component B particles. As a consequence of the effects of scale previously explained, increased pore size does not continue to produce improved ion-exchange capacity beyond a certain optimum X/D ratio.

As a further consideration it is also noticed that structural strength of the Component A particles is adversely affected by excessively large volume average pore diameter. Suitable margins of resin strength are necessary considering the handling procedures and operating pressures to which the ion-exchange resin are subjected during manufacture and use in ion-exchange chromatographic applications.

Preferred therefore under the conditions of the present invention are compositions having X/D ratios no greater than about 30. Highly preferably the X/D ratios are from about 5 to about 10. Optimum values of the X/D ratio will vary for differing resin materials, particle sizes, and operating conditions. Such optimum values within the limits stated may be easily identified by simple testing of a number of representative samples.

The term "volume average diameter" as used herein is synonymous with the term "median diameter" appearing in U.S. Pat. No. 4,101,460. When referring to particle size it relates to the statistical distribution of total particle volume with respect to varying particle size. One method used to determine the volume average diameter of particles involves determining the statistical median with respect to volume of the range of the particles' Martin's diameters present. The method is disclosed in U.S. Pat. No. 4,101,460, for which teaching said patent is incorporated herein by reference.

The term "volume average pore diameter" is a similar term well-known in the art relating to the statistical distribution of total pore volume of the macroporous resin with respect to varying pore size. The method employed herein for determining "volume average pore diameter" is the known technique of mercury porousimetry as described in "Advanced Experimental Techniques in Powder Metallurgy", Vol. 5, Plenum Press (1970).

The word "diameter" appearing in both terms should not be construed as indicating that either Component A or Component B particles are exactly spherical in shape or that the pores of Component A particles are of exactly circular cross-section. Photomicrographs indicate the particles are generally spherical shaped particles substantially lacking corners, edges and sharp projections and the pores are convoluted, tubulous, generally smooth surfaced ducts of curvate shape. When Component B is formed from ground ion-exchange resin however, projections, edges or corners are very likely to be present due to the grinding process which may tend to shatter individual ion-exchange resin particles. For statistical purposes however, it is assumed the particles and pores approximate spheres and cylindrical tubules thus giving rise to use of the term "diameter".

The composition of the invention further comprises a finely divided solid material, hereinafter referred to as Component B, comprising synthetic resin particles having a volume average diameter less than 0.1 micron and greater than about 0.005 micron, wherein the particles of Component B form an irreversibly attached monolayer on the available surface of Component A. These particles have ion-exchanging sites at least on the outer surface, preferably substantially throughout the entirety of a majority of the particles, which attract the available sites of Component A. Again, the material from which these particles are derived should be chosen so as to be insoluble in the solvents with which they may be contacted.

Most preferably, Component B comprises synthetic resin particles having a volume average diameter selected such that Component B particles fit into pores having a diameter less than about $0.3\mu$ (3000 Å). Component B most preferably has a volume average diameter from about 0.01 to about $0.08\mu$.

The term "available surface" refers to that surface of Component A which will come into contact with particles of Component B when Component A is contacted with a suspension of Component B. The available surface will be both the outer surface of that resin and the inner surface of the minute channels which permeate the structure of the resin and which have pore sizes sufficiently large to allow entry of Component B.

Component B particles further are defined by "size range" which means a range of particle sizes, the volume of which makes up at least about 90 percent of the total volume of Component B particles. Preferred in the instant invention is a size range from about one-half the volume average diameter of Component B to about twice the volume average diameter of Component B, that is, from about 0.0025 micron to about 0.2 micron.

Suitable materials from which the particles may be derived are the well-known synthetic polymeric ion-exchange resins. In addition to those resins specifically mentioned in the description of Component A above, amine-epichlorohydrin copolymers, graft polymers of styrene on polyethylene or polypropylene, and poly(2-chloromethyl-1,3-butadiene) resins are suitable. The resins may be of the gel or macroporous type or ion-exchange latex resins such as have been heretofore known and used by the art. Preferred for use in Component B is an ion-exchange latex resin having ion-exchanging sites substantially throughout the entirety of a majority of the particles. Ion-exchange latex resin may be prepared to be substantially monodisperse in particle size, thus obviating a need to carefully refine Component B particles as to particle size. When so characterized as "substantially monodisperse" the particles are of such substantially uniform size that the diameter range of such particles is within the hereinbefore defined size range. Preparation of such ion-exchange latex resins is well-known in the art having been described, for example, in U.S. Pat. No. 4,101,460.

The ion-exchanging sites of Component B particles may be anion- or cation-exchanging sites, depending upon the type of available sites found on Component A. When the available sites of Component A are anion-exchanging sites, the sites of Component B will be cation-exchanging sites and vice versa. The term "cation-exchanging sites" is meant to include chelating sites which are attracted to or form coordination complexes with the ion-exchanging sites of the other component. For example, aminocarboxylic acid groups are such chelating sites. The preparation of resins with such chelating sites is well-known in the art, for example, as described by Morris, U.S. Pat. No. 2,875,162 (1959), and Mock et al., U.S. Pat. No. 2,910,445 (1959). Such a chelating resin, commercially available, is Dowex® A-1 chelating resin.

Essentially equivalent specific ion-exchange capacities can be obtained by depositing relatively small Component B particles in relatively small Component A pores or by depositing relatively large Component B particles in relatively large Component A pores. It may easily be seen that a wide range of pore sizes are suitable for use according to the instant invention. Desirable qualities of the chromatographic composition may be enhanced by selectively employing suitably chosen sizes of Component B particles to correspond to the pore size of Component A particles. For example, ease of manufacture of the ion-exchange composition is increased by employing relatively large Component B particles that are easier to manufacture and handle, particularly when Component B particles are produced by grinding of commercially obtained ion-exchange resins, and by employing Component A particles having correspondingly large pore sizes.

To use Component A or Component B in a smaller particle size than is readily available, the available material may be reduced in size by conventionally known mechanical means such as ball mills, rod mills and the like. Selection of particles of a suitable size range for use in the invention may be also accomplished by well-known means such as screening through conventional sieves, suspending and settling in a liquid medium by centrifugation or similar means, or combinations thereof. Ordinarily, commercially available macroporous ion-exchange resin beads are suitable for use as Component A. Commercial ion-exchange resins with opposite ion-exchanging sites may be finely divided by the means described above to form Component B particles. Such finely divided ion-exchange resin may be refined as to particle size by ultra-centrifugation as is well-known in the art, in which case a distribution of particle sizes usually results. Alternatively, Component B particles may be ion-exchange latex particles which may be easily produced in a substantially monodisperse size as determined, for example, by comparison measurements from photomicrographs, or other means. Best performance is generally obtained using a latex to prepare a highly uniform monolayer of Component B particles.

The nature of the ion-exchanging sites on each component will be determined by the ultimate use for which an ion-exchange composition will be employed. Two main categories of ion-exchanging sites are anion- and cation-exchanging sites. These are further divided in the art into strong and weak base anion-exchanging sites and strong and weak acid and chelating cation-exchanging sites. Chelating sites have been described above. Strong base anion-exchanging sites are generally quaternary ammonium groups while weak base anion-exchanging sites are generally tertiary, secondary and primary amine functional groups. Strong acid cation-exchanging sites are generally sulfonate functional groups and weak acid cation-exchanging sites are generally carboxyl functional groups. Ion-exchange resins which contain these functional groups are known, respectively, as strong base and weak base anion-exchange resins, and strong acid and weak acid cation-exchange resins. Those with chelating sites are known as chelating resins.

In the ion-exchange composition of the invention, the two components may comprise any combination of two oppositely charged ion-exchange resins. Preferred, however, are combinations of: strong acid-strong base resins; strong acid-weak base resins; strong base-weak acid resins; and strong base-chelating resins. A highly preferred combination is one where Component A comprises a strong acid resin and Component B comprises a strong or weak base resin.

The ion-exchange composition is prepared by irreversibly attaching a monolayer of Component B particles to the available surface of Component A. One method is to contact a liquid suspension of Component B particles with the available surface of Component A as is taught in U.S. Pat. No. 4,101,460. An additional method is disclosed in U.S. Pat. No. 4,119,580 whereby the substrate particles are added to a dispersion of Component B particles in an aqueous solution of a multivalent salt. For said teaching U.S. Pat. Nos. 4,101,460 and 4,119,580 are incorporated herein by reference.

Like the compositions claimed in U.S. Pat. No. 4,101,460 the ion-exchange compositions of the instant invention have been found to be remarkably stable. The particles of Component B are irreversibly attached to the available surface of Component A such that a substantial number of Component B particles will not be displaced from the available surface of Component A by solutions of strong electrolytes or polyelectrolytes. For example, about 0.5 molar and preferably about 1.0 molar sodium hydroxide solution should not displace a substantial number of Component B particles, neither should shearing forces such as those encountered when a liquid passes through an ion-exchange bed at elevated flow rates displace a substantial number of Component B particles.

As previously explained the ion-exchange composition of the invention has been found to be useful in the well-known process of ion-exchange chromatography. One surprising advantage found in employing the composition of the instant invention is that equivalent separation of ions is obtainable while employing chromatographic columns of substantially reduced length compared to ion-exchange chromatographic processes utilizing ion-exchange compositions of the prior art. Such compact ion-exchange chromatographic columns are of themselves significant advances in the art. Additionally, it has been found that reduced volumes of eluent may be employed when using the instant composition while retaining equivalent or improved separation of ionic species compared with compositions of the prior art. Furthermore, in applications wherein a subsequent "stripper" column is employed to selectively suppress the effect of undesired ionic species introduced by the eluent, as is taught in U.S. Pat. No. 3,920,397, an additional advantage obtained in employing the compositions of the instant invention is increased lifetime of the material employed by the "stripper" column due to the reduced volumes of eluent required by operation of the ion-exchange column.

SPECIFIC EMBODIMENTS OF THE INVENTION

Example 1

An ion-exchange composition was formed according to the method described in U.S. Pat. No. 4,119,580. Component A was produced from about 10 grams of a rigid macroporous styrene-divinylbenzene copolymeric resin sold commercially as $10^6$ Å μ STYROGEL chromatographic packing resin. Measurements of photomicrographs determined the resin size to be from about 10 to about 30 microns with a volume average pore diameter as determined by mercury porousimetry of about 0.3 micron.

The Component A precursor was placed in a 1 liter three-necked flask containing 250 ml of methylene chloride and the flask equipped with a stirrer, condenser and an addition funnel. A solution made of 10 ml of chlorosulfonic acid in 250 ml of methylene chloride was placed in the addition funnel and slowly added with stirring to the resin slurry. Upon complete addition of the chlorosulfonic acid solution heating was begun and maintained for one-half hour to maintain a gentle reflux.

Heating was discontinued, the mixture cooled and 10 ml of water were slowly added to react with the excess chlorosulfonic acid. An additional 100 ml of water were added and the resulting mixture stirred for 15 minutes. The sulfonated beads were separated by filtration and washed in succession with 200 ml of methanol, methylene chloride and methanol.

Separation of fine particles was accomplished by slurring the sulfonated resin with water, allowing the heavier resin particles to settle and draining off substantially all of the water fraction. This process was repeated a total of three times. The remaining resin sediment was found upon microscopic examination to consist of resin particles of a uniform size almost entirely from 10 to 30 microns in diameter.

Filtration and final washing of the sediment with a saturated aqueous sodium carbonate solution produced Component A particles for use as the substrate of the invention.

Component B particles were formed in the following manner. Polyvinylbenzyl chloride latex seed resin containing about 5 percent by weight divinylbenzene crosslinking agent was contacted with excess dimethylethanolamine to form latex particles with active sites of the following formula:

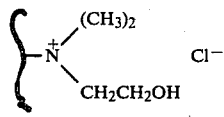

The latex was characterized as substantially monodisperse having a volume average diameter of about 0.05 micron as determined from measurements of photomicrographs of the resin, and the technique previously described in U.S. Pat. No. 4,101,460, and a solids content of about 10 percent by weight. In this example the X/D ratio was about 6.

The above-described ion-exchange latex resin was sonicated, i.e., exposed to high frequency sound waves in order to break down particle agglomeration. Approximately one-half milliliter of the deagglomerated resin was transferred to a small glass vial containing 10 milliliters of saturated aqueous sodium carbonate. The slurry was rapidly agitated with a disk on rod stirrer while 5 milliliters of a 50 percent slurry of Component A in saturated aqueous sodium carbonate was slowly added. The mixture was stirred for an additional 5 minutes. The stirrer was removed and the mixture shaken on a mechanical shaker at moderate speed for about 15 hours.

The vial was then centrifuged at slow speed for about 5 minutes to separate excess unattached ion-exchange latex resin from the desired two-component composition. The liquid fraction was decanted and the remaining sediment washed with saturated aqueous sodium carbonate and filtered. Microscopic examination of the completed composition indicated little damage to substrate particles had resulted from the process of attaching the latex monolayer.

Example 2

Preparation of Ion-Exchange Chromatographic Column

The ion-exchange composition of Example 1 was prepared as a 33 percent by volume slurry in saturated aqueous sodium carbonate for packing into a standard 2.8×100 mm type MB glass chromatograph column available commercially from Laboratory Data Control Corporation. The slurry was drawn into a plastic syringe and injected into the column. When packed the column was conditioned by flushing with an eluent comprising a two-component aqueous solution: 0.003 M $NaHCO_3$ and 0.0024 M $Na_2CO_3$ at a flow rate of 69 ml/hour for 15 minutes. The packed and conditioned column was then ready for use.

A stripper column was prepared comprised of a 2.8×300 mm glass chromatography column packed with a commercially available styrene-divinylbenzene copolymeric resin in the hydrogen ion form and from 400–200 U.S. mesh size (about 35–75 microns) sold as DOWEX 50W×16 ion-exchange resin. Eluent from the chromatograph column was directed through the stripper column for suppression of the response of the carbonate and bicarbonate ions in the eluent and then through a model CM-1A Chromatronix conductivity detector for detection of the separated ions. Full scale recorder deflection was set at 15μ Mho cm$^{-1}$.

Example 3

Chromatographic Separation

The packed and conditioned ion-exchange chromatographic column plus stripper column and conductivity detector prepared in Example 2 were used to separate and identify the anions of a standard aqueous anion solution comprising 3.3 parts per million (ppm) F$^-$, 4 ppm Cl$^-$, 10 ppm NO$_2^-$, 54 ppm PO$_4^{-3}$, 10 ppm Br$^-$, 34 ppm NO$_3^-$ and 50 ppm SO$_4^{-2}$.

About 50 μl of this standard was injected into the column and eluted with a total of 23 ml of the eluent previously described in Example 2 (0.003 M $NaHCO_3$ and 0.0024 M $Na_2CO_3$) at a flow rate of 69 ml/hour and at a pressure of about 350 psig (24.1 bar).

Figure 2:
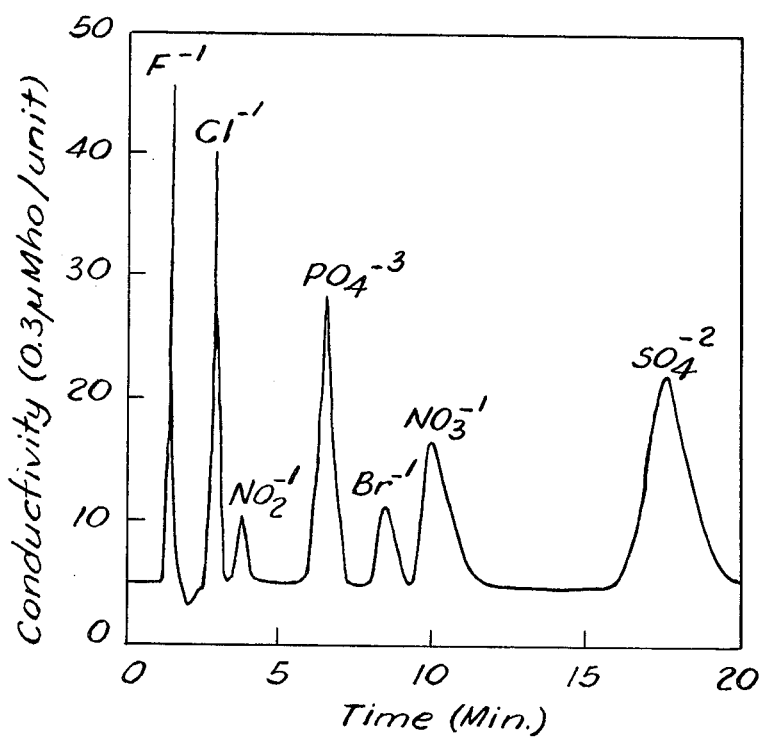
FIG. 2 is a chromatogram of the anions of FIG. 1 performed under comparable conditions being FIG. 3 of U.S. Pat. No. 4,119,580.

The resulting chromatogram is shown in FIG. 1. This chromatogram may be compared with the chromatogram of FIG. 2, corresponding to FIG. 3 of U.S. Pat. No. 4,119,580, obtained using a 2.8×500 mm column charged with the ion-exchange composition described and claimed in U.S. Pat. No. 4,101,460. Comparable pressure and other conditions were employed for obtaining the two chromatograms except that the instant column is only 1/5 as long as that previously used, and the flow rate of eluent is ½ of the flow rate previously employed. Additional differences in experimental technique include use of a smaller standard anion sample, 50 μl instead of 100 μl, and greater recorder sensitivity, full-scale deflection of 15 μ Mho cm$^{-1}$ instead of 30 μ Mho cm$^{-1}$.

Comparison of the two chromatograms shows nearly identical overall performance yet column length when employing the instant composition is substantially shortened. It is immediately apparent that the instant invention allows for a more compact and hence more economical ion-exchange chromatography system that provides equivalent performance with previously known systems.

Moreover, by utilizing lower rates of elution as is possible with the composition of the instant invention, the life of the stripper column is increased so that regeneration of the stripper column is necessary approximately one-half as often as with previous compositions.

I claim:

1. A composition of matter for exchanging ions comprising:
   Component A, a substrate which consists essentially of macroporous synthetic resin, having ion-exchanging sites at least on its available surface, having a volume average pore diameter of X; and
   Component B, finely divided synthetic resin particles having a volume average diameter (D) less than 0.08 micron and greater than 0.005 micron and having, at least on their outer surfaces, ion-exchanging sites which attract available sites of Component A; wherein the particles of Component B are irreversibly attached as a monolayer to the available surface of Component A;
   provided that, the ratio X/D is from about 4 to about 30.

2. The composition of claim 1 wherein Component A comprises finely divided macroporous particles of about 2 to about 75 microns particle size which have ion-exchanging sites at least on their available surface and Component B particles have ion-exchanging sites substantially throughout the entirety of a majority of Component B particles.

3. The composition of claim 1 wherein the particle size of Component A particles is about 2 to about 30 microns.

4. The composition of claim 1 wherein the size range of Component B particles is from about 0.0025 micron to about 0.2 micron.

5. The composition of claim 1 wherein the volume average diameter of Component B particles is from about 0.01 to about 0.08 micron.

6. The composition of claim 1 wherein the ratio X/D is from about 5 to about 10.

7. The composition of claim 1 or 2 wherein Component A comprises a poly(vinylaromatic) resin.

8. The composition of claim 1 wherein Component B particles are ion-exchange latex resin particles.

9. A chromatographic column packed with the composition of claim 1.

* * * * *

UNITED STATES PATENT AND TRADEMARK OFFICE
CERTIFICATE OF CORRECTION

PATENT NO. : 4,351,909

DATED : September 28, 1982

INVENTOR(S) : Timothy S. Stevens & William Rich

It is certified that error appears in the above—identified patent and that said Letters Patent is hereby corrected as shown below:

Title page, under inventor, joint inventorship was not shown. "Inventor: Timothy S. Stevens" should read -- Inventor: Timothy S. Stevens & William Rich --.

Column 1, line 5, "CROSSREFERENCE TO RELATED" should read -- CROSS-REFERENCE TO RELATED --.

Column 3, line 3, "that pore" should read -- than pore --.

Column 9, line 29, "0.08 micron" should read -- about 0.08 micron --.

Signed and Sealed this

Twelfth Day of April 1983

[SEAL]

Attest:

GERALD J. MOSSINGHOFF

Attesting Officer     Commissioner of Patents and Trademarks